US008943908B2

United States Patent
Liu et al.

(10) Patent No.: US 8,943,908 B2
(45) Date of Patent: Feb. 3, 2015

(54) IMPERCEPTIBLE MOTION SENSING DEVICE HAVING CONDUCTIVE ELASTOMER

(71) Applicant: Seda Chemical Products Co., Ltd., New Taipei (TW)

(72) Inventors: Yu-Wei Liu, Taipei (TW); Ke-Yuan Wu, Zhongli (TW); Wei-Kuan Wang, Taipei (TW)

(73) Assignee: Seda Chemical Products Co., Ltd., New Taipei (TW)

( * ) Notice: Subject to any disclaimer, the term of this patent is extended or adjusted under 35 U.S.C. 154(b) by 160 days.

(21) Appl. No.: 13/781,955

(22) Filed: Mar. 1, 2013

(65) Prior Publication Data

US 2014/0026682 A1 Jan. 30, 2014

(30) Foreign Application Priority Data

Jul. 27, 2012 (TW) .............................. 101214606 U

(51) Int. Cl.
*G01L 1/04* (2006.01)
*G01L 1/22* (2006.01)
*G01L 1/06* (2006.01)
*G01L 1/20* (2006.01)

(52) U.S. Cl.
CPC .... *G01L 1/06* (2013.01); *G01L 1/20* (2013.01)
USPC ............ 73/862.637; 73/862.042; 73/862.046; 73/172

(58) Field of Classification Search
USPC ........ 73/862.041–862.046, 862.68, 768, 172, 73/849, 862.381, 862.632, 862.637
See application file for complete search history.

(56) References Cited

U.S. PATENT DOCUMENTS

| | | | | |
|---|---|---|---|---|
| 4,394,773 A * | 7/1983 | Ruell | .............................. | 382/124 |
| 4,492,949 A * | 1/1985 | Peterson et al. | .............. | 338/114 |
| 4,555,954 A * | 12/1985 | Kim | ......................... | 73/862.046 |
| 5,799,533 A * | 9/1998 | Seki et al. | ......................... | 73/172 |
| 6,369,804 B1 * | 4/2002 | Sandbach | ....................... | 345/173 |
| 6,437,258 B1 * | 8/2002 | Sandbach | ................... | 178/18.05 |
| 7,658,119 B2 * | 2/2010 | Loeb et al. | ............... | 73/862.046 |
| 7,814,801 B2 * | 10/2010 | Inamori | .......................... | 73/849 |
| 7,849,751 B2 * | 12/2010 | Clark et al. | ...................... | 73/768 |
| 7,938,025 B2 * | 5/2011 | Shimomoto et al. | ...... | 73/862.046 |
| 8,161,826 B1 * | 4/2012 | Taylor | ...................... | 73/862.044 |
| 8,181,540 B2 * | 5/2012 | Loeb et al. | ................. | 73/862.59 |
| 8,234,929 B2 * | 8/2012 | Clark et al. | ..................... | 73/776 |
| 8,359,931 B2 * | 1/2013 | Nishiwaki | ....................... | 73/846 |

(Continued)

*Primary Examiner* — Lisa Caputo
*Assistant Examiner* — Jonathan Dunlap
(74) *Attorney, Agent, or Firm* — Bacon & Thomas, PLLC

(57) ABSTRACT

The present invention is to provide an imperceptible motion sensing device, which includes a non-conductive elastomer made of a pliable and elastic non-conductor (e.g., polyurethane) and having a bumpy side formed with at least one sunken portion thereon, at least one conductive fiber positioned in the at least one sunken portion respectively (e.g., by sewing), and a conductive elastomer made of a pliable and elastic conductor (e.g., a conductive foam or conductive rubber) and provided on the bumpy side of the non-conductive elastomer. When the sensing device is compressed by an external force, corresponding portions of the conductive elastomer and the non-conductive elastomer are compressed and deformed, causing contact and hence electrical connection between the conductive elastomer and the at least one conductive fiber. Thus, the imperceptible motion sensing device not only provides more accurate and more sensitive signal detection, but also ensures consistent performance even after long-term use.

5 Claims, 4 Drawing Sheets

(56) References Cited

U.S. PATENT DOCUMENTS

| | | | |
|---|---|---|---|
| 8,393,229 B2* | 3/2013 | Tao et al. | 73/862.046 |
| 8,573,069 B2* | 11/2013 | Nishiwaki | 73/862.474 |
| 8,640,550 B2* | 2/2014 | Nishiwaki | 73/846 |
| 8,640,551 B2* | 2/2014 | Nishiwaki | 73/846 |
| 8,656,790 B2* | 2/2014 | Amirouche | 73/862.041 |
| 8,661,915 B2* | 3/2014 | Taylor | 73/862.044 |
| 8,800,386 B2* | 8/2014 | Taylor | 73/862.044 |
| 8,820,173 B2* | 9/2014 | Clark et al. | 73/768 |

* cited by examiner

IMPERCEPTIBLE MOTION SENSING DEVICE HAVING CONDUCTIVE ELASTOMER

FIELD OF THE INVENTION

The present invention relates a sensing device, more particularly to an imperceptible motion sensing device applicable to various products in a home environment (e.g., mattresses, seat cushions, table and chair leg cushions, and even clothes) for monitoring an elderly person's activities at home in a way, not only capable of effectively reducing the elderly person's psychological resistance, but also providing more accurate and sensitive signal detection and, at the same time, ensuring consistent performance even after long-term use.

BACKGROUND OF THE INVENTION

Due to the decline of birth rates and improvements of the medical environments, the percentage of the elderly population in a great number of countries has risen significantly, and so has the prevalence of chronic diseases. As a result, the need for medical care services increases continuously. With the development of such services, techniques for monitoring a person's body movements at home have evolved so much that a medical care service provider can now obtain real-time and comprehensive information about the activities and states (e.g., breathing, body movements, the gravity center of the body, and body postures) of a monitored person (e.g., an elderly person or one with a chronic disease) in order to provide the person with the necessary medical care services rapidly and proactively.

Today, a sensing device as shown in FIG. 1 is commercially available for a medical care service provider to keep track of a monitored person's various activities at home (e.g., when and how the person gets on or off the bed, sleeps, moves, and is seated). Referring to FIG. 1, the sensing device 1 includes two layers of elastic structures 11, a plurality of first conductive fibers 12 (e.g., conductive metal fibers, conductive metal compound fibers, or conductive carbon black fibers), and a conductive fabric 13. The first conductive fibers 12 are sewn on the elastic structures 11 and exposed on their opposing sides respectively. The conductive fabric 13 is woven from second conductive fibers 131 and a common yarn 132 (or from a mixed yarn spun from the second conductive fibers 131 and common fibers) and is provided between the elastic structures 11. When the sensing device 1 is compressed by an external force, the elastic structures 11 are compressed and deformed such that the first conductive fibers 12 contact with and are electrically connected to the second conductive fibers 131 in the conductive fabric 13, forming a plurality of contact points and a plurality of sensing resistors. A control module (not shown) electrically connected to the first conductive fibers 12 or the conductive fabric 13 of the sensing device 1 can generate signals according to the relationships between the total resistance of the sensing resistors, the operating voltage of the control module, the magnitude and area of the pressure applied to the sensing device 1, and the number of the contact points. By connecting the control module to another electronic device (not shown) in a wired manner or wirelessly, a medical care service provider can process and analyze the signals by way of the electronic device and thus be informed of the monitored person's activities.

The sensing device 1 is applicable to various products in a home environment (e.g., mattresses, seat cushions, table and chair leg cushions, and even clothes) to enable monitoring of a monitored person's activities at home, and thanks to its non-invasiveness and low constraint, the sensing device 1 can effectively reduce the monitored person's psychological resistance. In addition, the sensing device 1 has such advantages as lightweight, structural simplicity, pliability, ease of use, and high comfort. Hence, in the field of home medical care services, the sensing device 1 has gradually become an important technique for use by a variety of monitoring apparatuses.

The inventor of the present invention has long been engaged in research and development related to medical care, paying close attention to market reactions and analyzing user feedbacks carefully. In the process, the inventor has found that, despite the foregoing advantages, the design of the sensing device 1 still has room for improvement. Referring back to FIG. 1, the conductive fabric 13, which is woven from the second conductive fibers 131 (e.g., conductive metal fibers or conductive metal compound fibers) and the common yarn 132, may form a projecting pointed portion 131a after repeated bending. As the pointed portion 131a rises above the plane where the conductive fabric 13 lies, it is very likely that the pointed portion 131a will contact with the first conductive fibers 12 even if the sensing device 1 is not subjected to an external force. Should that happen, the first conductive fibers 12 will be electrically connected to the conductive fabric 13, causing erroneous electrical connection signals. Further, with the conductive fabric 13 being woven from the second conductive fibers 131 (e.g., conductive metal fibers or conductive metal compound fibers) and the common yarn 132, friction between the conductive fabric 13 and the elastic structures 11 may cause the common yarn 132 to produce lint balls 132a on the surface of the conductive fabric 13 after long-term use. The lint balls 132a may correspond in position to the first conductive fibers 12 and, due to the fact that the lint balls 132a are formed by the non-conductive common yarn 132, may hinder electrical connection between the first conductive fibers 12 and the second conductive fibers 131 when the sensing device 1 is compressed by an external force, thereby rendering the sensing device 1 less sensitive in use.

According to the above, although the conventional sensing device 1 can effectively reduce a monitored person's psychological resistance and advantageously provide convenient and comfortable use, the material properties of the conductive fabric 13 tend to lower the accuracy and sensitivity of detection signals after the sensing device 1 is used for some time, thus leaving something to be desired in terms of durability. Therefore, the issue to be addressed by the present invention is to modify the structural design of the sensing device 1, with the intention of increasing the accuracy and sensitivity of the detection signals of the sensing device 1.

BRIEF SUMMARY OF THE INVENTION

In view of the drawbacks of the conventional sensing devices, the inventor of the present invention incorporated years of practical experience into designing, made continuous improvements, and finally succeeded in developing an imperceptible motion sensing device having a conductive elastomer as disclosed herein. The present invention is intended to increase the accuracy and sensitivity of the detection signals of a sensing device and thereby enhance the durability of the sensing device.

It is an object of the present invention to provide an imperceptible motion sensing device having a conductive elastomer, wherein the sensing device includes a non-conductive elastomer and at least one conductive fiber in addition to the conductive elastomer. The non-conductive elastomer is made of a pliable and elastic non-conductor (e.g., polyurethane)

and is bumpy on one side, forming at least one sunken portion. The at least one conductive fiber is positioned in the at least one sunken portion respectively (e.g., by sewing). The conductive elastomer is made of a pliable and elastic conductor (e.g., a conductive foam or conductive rubber) and is provided on the bumpy side of the non-conductive elastomer. When the sensing device is compressed by an external force, corresponding portions of the conductive elastomer and the non-conductive elastomer are compressed and deformed, causing contact and hence electrical connection between the conductive elastomer and the at least one conductive fiber. As the present invention uses the conductive elastomer in place of the conductive fabrics in the conventional sensing devices, the various problems caused by the conductive fabrics can be prevented, such as the generation of false contact signals when, in the absence of an external force compressing a conventional sensing device, some broken or protruding conductive fibers in the conductive fabric of the sensing device contact with the conductive fibers sewn on a non-conductive elastomer; and the generation of lint balls from the common fibers in the conductive fabric (woven from conductive fibers and the common fibers) of a conventional sensing device after long-term use such that, when the sensing device is compressed by an external force, the lint balls hinder electrical connection between the conductive fibers in the conductive fabric and the conductive fibers sewn on a non-conductive elastomer. The imperceptible motion sensing device having a conductive elastomer as disclosed herein not only provides more accurate and more sensitive signal detection in comparison with the conventional sensing devices, but also ensures consistent performance even after long-term use; in other words, the disclosed sensing device is more durable than the prior art devices.

BRIEF DESCRIPTION OF THE SEVERAL VIEWS OF THE DRAWINGS

The structure as well as a preferred mode of use, further objects, and advantages of the present invention will be best understood by referring to the following detailed description of some illustrative embodiments in conjunction with the accompanying drawings, in which.

DETAILED DESCRIPTION OF THE INVENTION

Figure 2:
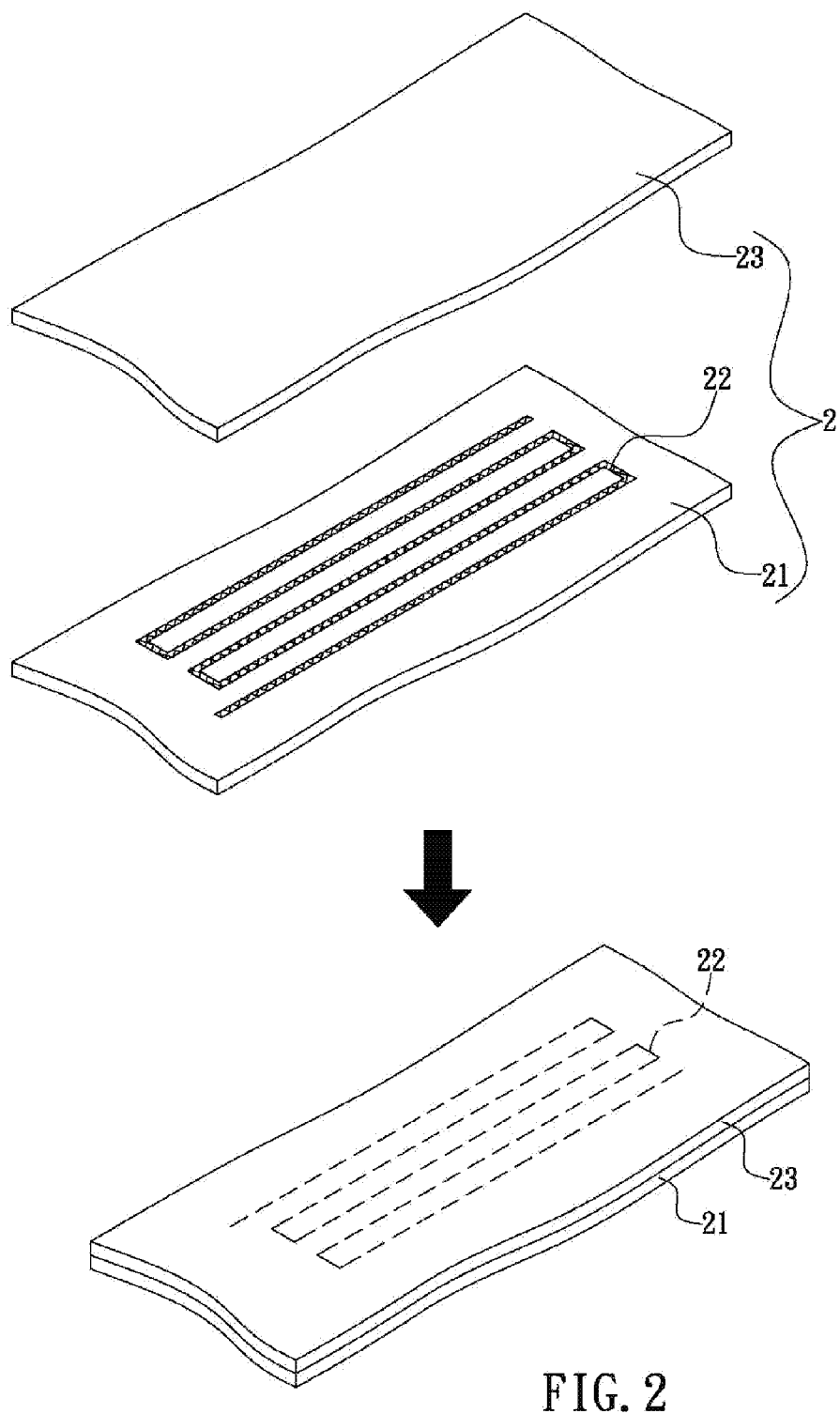
FIG. 2 is a schematic overall structural diagram of the first preferred embodiment of the present invention.
Figure 3:
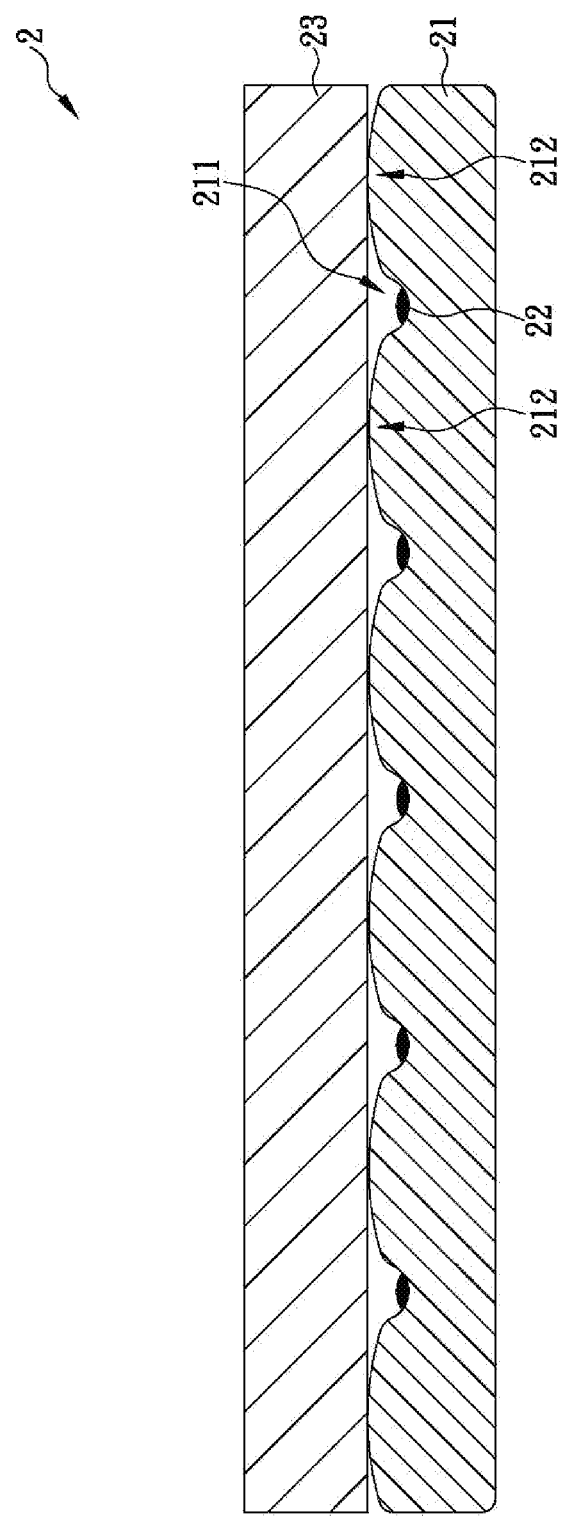
FIG. 3 is a schematic sectional view of the first preferred embodiment of the present invention.

The present invention discloses an imperceptible motion sensing device having a conductive elastomer. In the first preferred embodiment of the present invention as shown in FIGS. 2 and 3, the sensing device 2 includes a non-conductive elastomer 21, at least one conductive fiber 22, and a conductive elastomer 23. The non-conductive elastomer 21 is made of a foamed material (e.g., polyurethane) but is not necessarily so. The non-conductive elastomer 21 may also be made of other pliable and elastic non-conductors. In the first preferred embodiment of the present invention, the conductive fiber 22 is sewn on the non-conductive elastomer 21, and with the non-conductive elastomer 21 being made of an elastically deformable material, the conductive fiber 22 tightly gathers certain parts of the non-conductive elastomer 21 while being sewn thereto. As a result, the non-conductive elastomer 21 is given a bumpy surface. More specifically, the parts of the non-conductive elastomer 21 that correspond to the conductive fiber 22 form sunken portions 211, whereas the other parts of the non-conductive elastomer 21 form raised portions 212 relative to the sunken portions 211. It should be pointed out that the bumpy surface of the non-conductive elastomer 21 is not necessarily formed by holding certain parts of the non-conductive elastomer 21 tightly together with the conductive fiber 22. A manufacturer may design and produce the non-conductive elastomer 21 as having a bumpy surface in the first place and then position the conductive fiber 22 at the sunken portions 211 on the surface of the non-conductive elastomer 21 by sewing, adhering, or other positioning means. In short, a manufacturer may vary the way in which the conductive fiber 22 is positioned and the design of the non-conductive elastomer 21 as appropriate.

Figure 4:
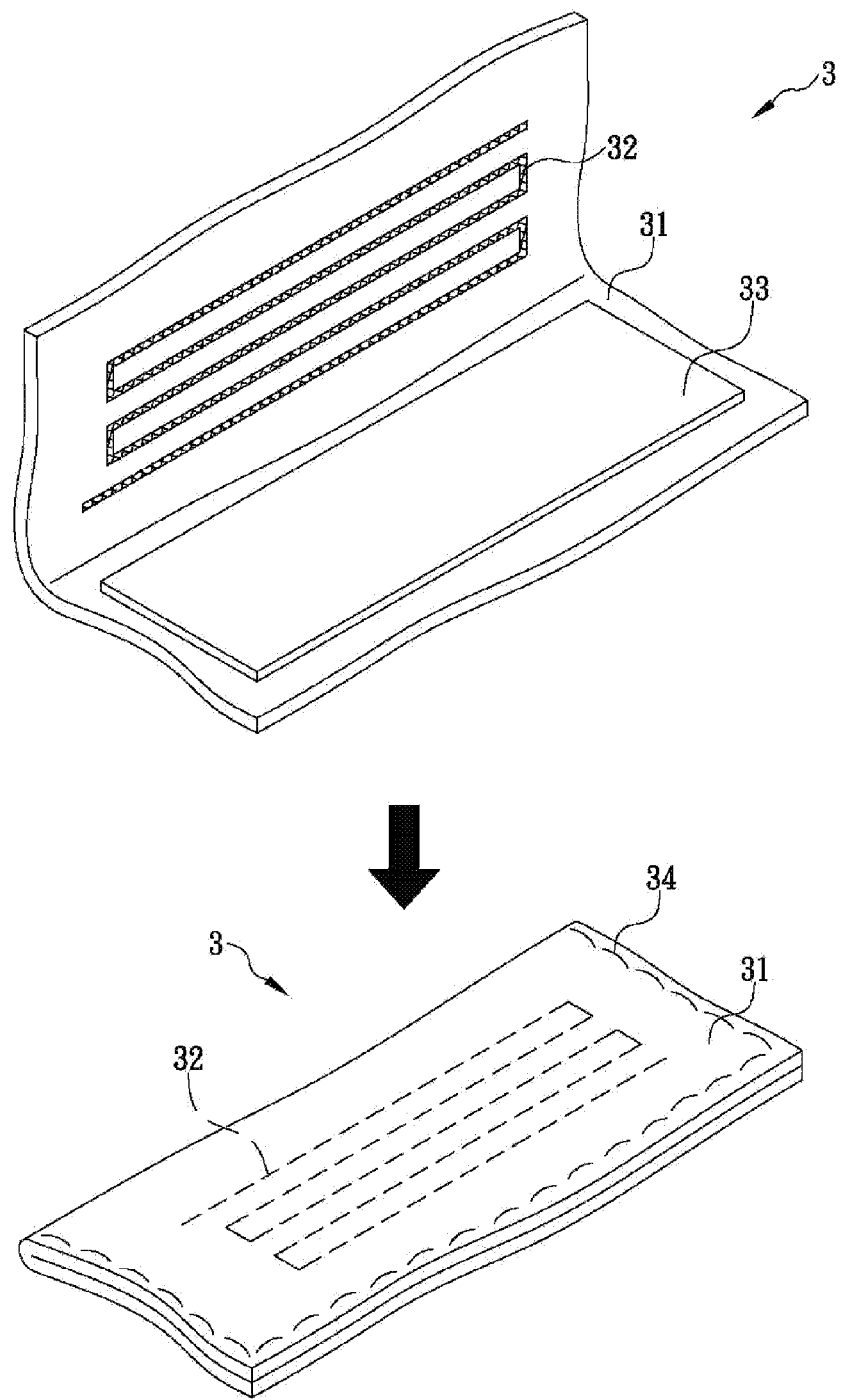
FIG. 4 is a schematic overall structural diagram of the second preferred embodiment of the present invention.

The conductive elastomer 23 is made of a pliable and elastic conductor (e.g., a conductive foam or conductive rubber) and is provided on the bumpy side of the non-conductive elastomer 21. In the first preferred embodiment of the present invention, the conductive elastomer 23 and the non-conductive elastomer 21 are adhered together along their peripheries, but the present invention is not limited to such an arrangement. Referring to FIG. 4 for the second preferred embodiment of the present invention, a manufacturer may alternatively design a non-conductive elastomer 31 of a relatively large area and sew the conductive fiber 32 to certain parts of one side of the non-conductive elastomer 31, such that the parts of the non-conductive elastomer 31 that correspond to the conductive fiber 32 become bumpy. Following that, a conductive elastomer 33 of a relatively small area is placed over another part of the aforesaid side of the non-conductive elastomer 31. By folding in half, the non-conductive elastomer 31 is turned into two connected sheets respectively attached to two opposite sides of the conductive elastomer 33. The folded assembly is then sewn along its periphery with a cotton thread 34 to form the sensing device 3. In this case, the non-conductive elastomer 31 constitutes the main body of the sensing device 3 and receives the conductive elastomer 33 therein. Thus, the conductive elastomer 33 is also securely positioned on the bumpy side of the non-conductive elastomer 31. By the same token, a manufacturer may produce the non-conductive elastomer 31 as two separate sheets, sandwich the conductive elastomer 33 in between them, and seal the two sheets of the non-conductive elastomer 31 together around their peripheries to produce an equivalent result. All equivalent changes or modifications easily conceivable by a person skilled in art who has perused the disclosure of the present specification should fall within the scope of the present invention.

Figure 1:
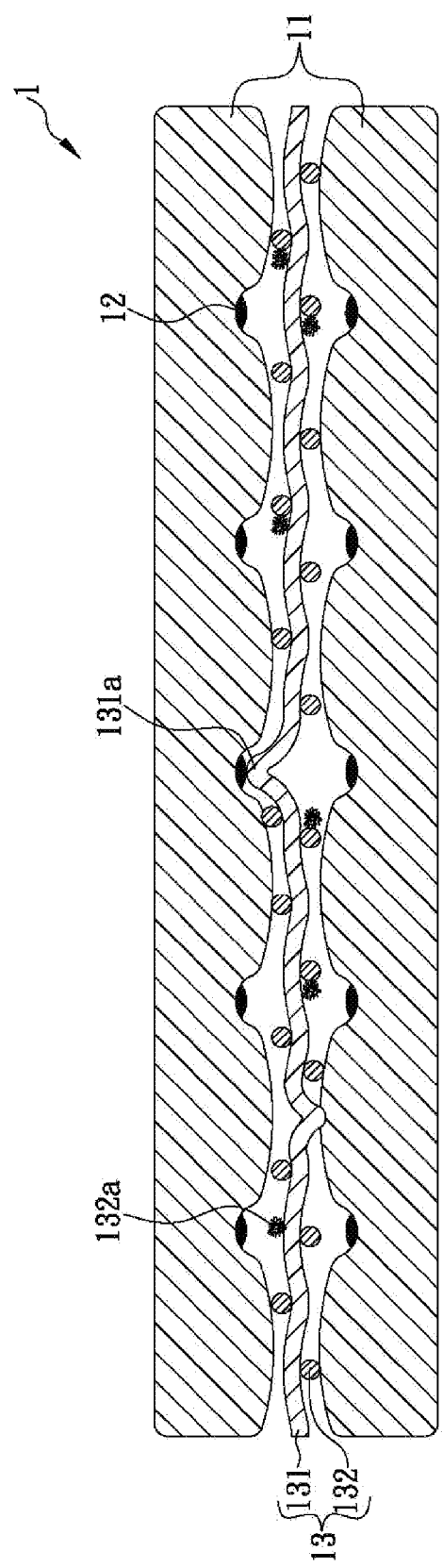
FIG. 1 is a schematic sectional view of a conventional sensing device.

Referring back to FIG. 3, when the sensing device 2 is not compressed by an external force, the conductive elastomer 23 lies against the raised portions 212 on the surface of the non-conductive elastomer 21 and is therefore spaced from the conductive fiber 22 positioned in the sunken portions 211. Once the sensing device 2 is compressed by an external force, corresponding portions of the conductive elastomer 23 and the non-conductive elastomer 21 undergo compression and deformation that bring the conductive elastomer 23 into contact and electrical connection with the conductive fiber 22. As the present invention uses the conductive elastomer 23 in lieu of the conductive fabric in a conventional sensing device (e.g., the conductive fabric 13 shown in FIG. 1), the sensing device 2 when used in signal detection can effectively avoid the various problems associated with the use of the conductive fabric, preventing the generation of false contact signals and a lowering of sensitivity after long-term use. It can be known from the foregoing that the sensing device 2 of the present invention provides more accurate and more sensitive signal detection than the conventional sensing devices and can perform consistently well after it is used for a long time. The durability of the sensing device 2 is therefore greatly enhanced as compared with the prior art devices.

The embodiments described above are but the preferred embodiments of the present invention and are not restrictive of the technical features of the present invention. All changes or modifications readily conceivable by a person skilled in the art should be encompassed by the appended claims. It is understood that applications of the present invention are by no means limited to the disclosed embodiments, for the present invention is equally applicable to, for example, the buttons of various electronic apparatuses (e.g., doorbells at home entrances and notification bells for use in conference rooms). Hence, the fields of application of the present invention do not constitute a limitation on the present invention. All alternative uses and modifications easily conceivable by a person of skill in the art should fall within the scope of the claims of the present invention.

What is claimed is:

1. An imperceptible motion sensing device having a conductive elastomer, comprising:
    a non-conductive elastomer made of a pliable and elastic non-conductor and having a bumpy side forming at least a sunken portion;
    at least a conductive fiber respectively positioned in the at least a sunken portion; and
    the conductive elastomer made of a pliable and elastic conductor and provided on the bumpy side of the non-conductive elastomer such that, when the sensing device is compressed by an external force, corresponding portions of the conductive elastomer and the non-conductive elastomer are compressed and deformed, bringing the conductive elastomer into contact and electrical connection with the at least a conductive fiber.

2. The sensing device of claim 1, wherein the at least a conductive fiber is respectively sewn to the at least a sunken portion.

3. The sensing device of claim 2, wherein the non-conductive elastomer and the conductive elastomer are connected together.

4. The sensing device of claim 2, wherein both the non-conductive elastomer and the conductive elastomer are sheet-like, the non-conductive elastomer forming two sheets which are respectively attached to two opposite sides of the conductive elastomer and are peripherally sealed together such that the conductive elastomer is received between the two sheets formed by the non-conductive elastomer.

5. The sensing device of claim 4, wherein the two sheets formed by the non-conductive elastomer are sewn together around peripheries thereof with a thread.

\* \* \* \* \*